United States Patent [19]

Goodin et al.

[11] Patent Number: 4,928,693
[45] Date of Patent: May 29, 1990

[54] PRESSURE MONITOR CATHETER

[75] Inventors: Richard L. Goodin, Blaine; Mark A. Rydell, Golden Valley; Rick L. Shockey, Eagan, all of Minn.

[73] Assignee: Schneider (USA), Inc., Minneapolis, Minn.

[21] Appl. No.: 322,362

[22] Filed: Mar. 13, 1989

[51] Int. Cl.$^5$ .............................................. A61B 5/00
[52] U.S. Cl. .................................... 128/637; 128/674; 128/772; 604/280
[58] Field of Search ................. 128/343, 344, 348.1, 128/656–658, 637, 672–675, 748, 772; 604/43, 53, 96, 101, 102, 280, 281, 283; 606/192, 194

[56] References Cited

U.S. PATENT DOCUMENTS

| | | | |
|---|---|---|---|
| 4,168,703 | 9/1979 | Kenigsberg | 128/748 |
| 4,545,390 | 10/1985 | Leary | 128/657 |
| 4,762,129 | 8/1988 | Bonzel | 128/344 |

Primary Examiner—Randall L. Green
Assistant Examiner—Randy Shay
Attorney, Agent, or Firm—Haugen and Nikolai

[57] ABSTRACT

A blood pressure monitoring catheter for use in a Monorail TM intravascular system for measuring the pressure gradient across a stenotic lesion. It comprises an elongated, flexible, plastic, extruded, tubular member having a guidewire port extending through the wall thereof a short distance proximal to the distal end of the tubular member to intersect with a lumen which extends to the distal end. The second lumen runs the entire length of the tubular member from its distal end to its proximal end. The proximal end of the blood pressure monitor catheter is fitted to a molded plastic hub to facilitate the attachment of the catheter to the blood pressure measuring apparatus with which the catheter is to be used.

3 Claims, 2 Drawing Sheets

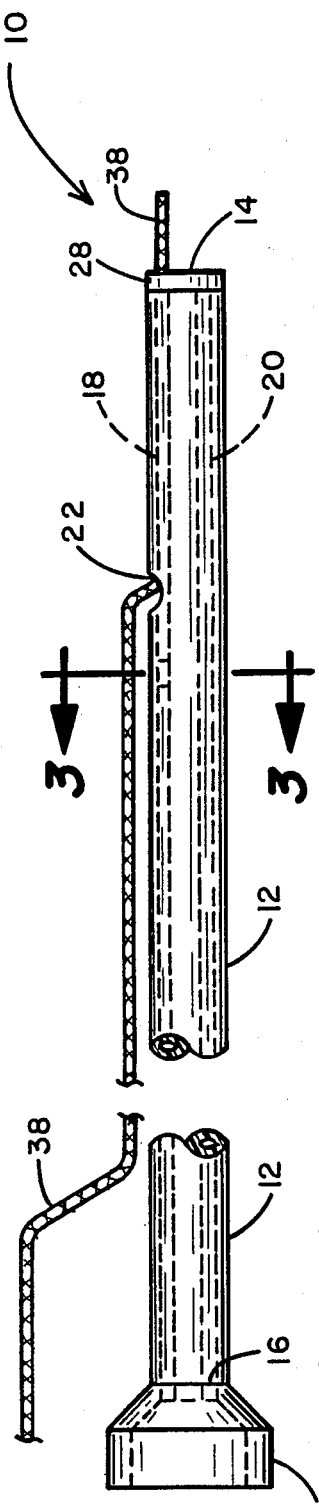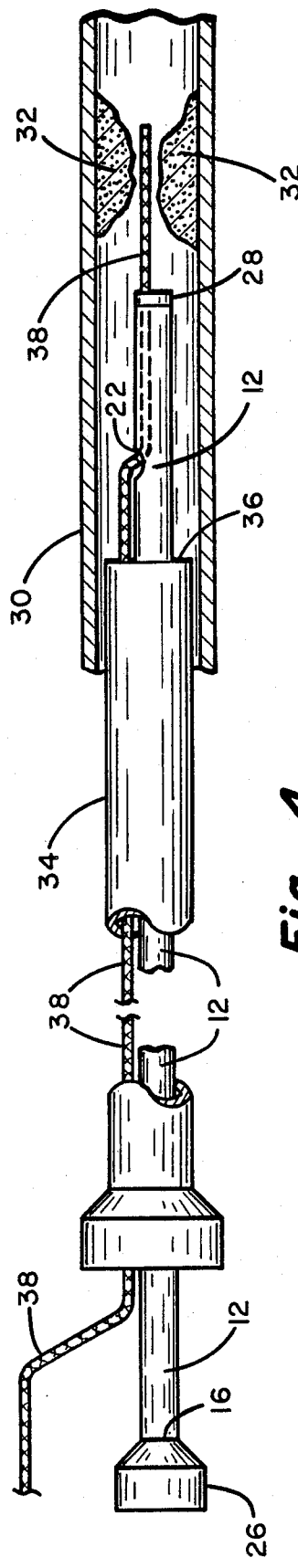

PRESSURE MONITOR CATHETER

BACKGROUND OF THE INVENTION

1. Field of the Invention:

This invention relates generally to surgical apparatus for use in the conduct of transluminal angioplasty or transluminal angiography procedures, and more particularly to the design of a blood pressure monitoring catheter especially designed for use in a Monorail TM type catheter system.

2. Discussion of the Prior Art:

In diagnosing and treating coronary artery disease, a technique called transluminal angiography may first be used to assess the extent and nature of the buildup of stenotic lesions within the vascular system. One important parameter useful in such assessment is the pressure gradient across a lesion. When the gradient is low, it is known that the lesion may not be seriously occluding the blood vessel. Where, however, the pressure gradient is high, it is known that the occlusion is significant and a candidate for immediate treatment.

One method of treatment of stenotic lesions in the vascular system is the use of so-called transluminal balloon angioplasty. In carrying out this procedure, an elongated, flexible, plastic catheter having an inflatable expander member proximate its distal tip is introduced at an appropriate site in the vascular system, usually in the femoral artery, and routed through the system to the site of the lesion to be treated. Once the uninflated expander is positioned across the lesion to be treated, an appropriate fluid is introduced into the proximal end of the catheter and it flows to inflate the balloon and compress the stenotic lesion against the walls of the blood vessel.

Two types of catheter systems are recognized in the art. The first is referred to as an over-the-wire catheter in which the catheter has a lumen extending its entire length from its distal end to its proximal end. Following the insertion of a guide catheter through the vascular system such that its distal end is located near the site to be treated, a guidewire is routed through the guide catheter and by manipulating the proximal end of the guidewire, an attempt is made to cause its distal end to cross the stenotic lesion to be treated. Following that, a balloon angioplasty catheter is fitted over the guidewire by having the guidewire pass through the lumen which runs the length of the catheter. These over-the-wire catheters have proven somewhat difficult to work with, especially when it comes to the need to exchange one working catheter for another. Moreover, because the guidewire is totally contained within the entire length of the working catheter, a relatively high frictional resistance tends to be present when advancing or retracting the working catheter relative to the guidewire. In fact, because of this frictional drag, it has happened that during an exchange maneuver, the guidewire is actually dislodged from its site across the stenotic lesion, thus requiring the surgeon to again go through a repositioning procedure.

To obviate certain of the problems associated with the over-the-wire catheter system, a subsidiary of applicant's assignee has developed a Monorail TM catheter system. Here, rather than running a guidewire completely along the interior lumen of the working catheter, a relatively short tubular segment is provided near the distal end of the working catheter for receiving the guidewire. Thus, rather than being totally enclosed with the wall of the working catheter over its entire length, in the Monorail TM catheter system, only a very short length of tubing surrounds the guidewire near the distal end of the working catheter. The guidewire then extends parallel to and along side the outer diameter of the working catheter as the two extend in the proximal direction through the guiding catheter. Details of the Monorail TM catheter construction are set out in the Bonzel U.S. Pat. No. 4,762,129, and those desiring further information relative to the overall features and advantages of Monorail TM catheters are referred to that patent.

The present invention is directed to a blood pressure monitoring catheter especially designed for use in a Monorail TM catheter system for assessing the pressure gradient across a stenotic lesion. The blood pressure monitoring catheter of the present invention thus comprises an elongated, flexible, plastic, bi-lumen, extruded, tubular member having a guidewire port extending through the wall thereof to intersect with one of the two lumens, the port being a relatively short distance proximal of the distal end of the tubular member. A plug is inserted into this one lumen at a point proximal of the guidewire port. The other lumen of the bi-lumen catheter runs the entire length of the tubular member from its distal end to its proximal end. The proximal end is fitted with a molded plastic hub to facilitate the attachment of the catheter to the auxiliary equipment used to measure, monitor and record blood pressure readings.

In use, once a guidewire has been positioned across the stenotic lesion and it is desired to take a blood pressure measurement, the proximal end of the guidewire may be fitted into the distal end of the first lumen and fed through it until the guidewire exits the guidewire port. Holding on to the proximal end of the guidewire, the physician may push the blood pressure monitoring catheter through the guide catheter and, in doing so, the blood pressure monitoring catheter will ride along the guidewire until its distal end is on one side or the other of the stenotic lesion. The proximal end of the blood pressure monitoring catheter is then connected to the blood pressure measuring equipment and a first reading taken. The blood pressure monitoring catheter is then repositioned on the opposite side of the stenotic lesion and a second reading is taken. Having the two readings, the gradient across the stenotic lesion is determined.

Alternatively, the catheter may include two blood pressure measuring lumens, one exiting the distal end of the catheter and the other ending proximally a predetermined distance from the distal end and with a port extending through the wall of the catheter in fluid communication with the shorter lumen. Readings can be simultaneously taken through both lumens without moving the catheter.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

FIG. 1 is a side elevation of a blood pressure monitoring catheter in accordance with the present invention;

FIG. 2 is a distal end view of the blood pressure monitoring catheter of FIG. 1;

FIG. 3 is a cross-sectional view of the catheter taken along lines 3—3 in FIG. 1;

FIG. 4 is a side elevation of the catheter in situ; and

DESCRIPTION OF THE PREFERRED EMBODIMENT

Figure 5:
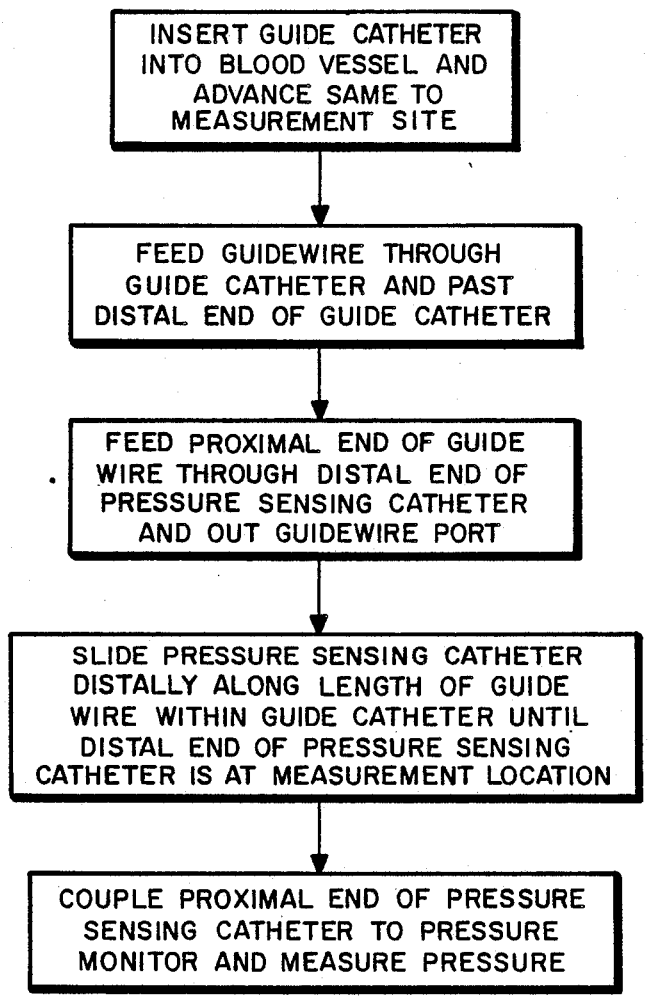
FIG. 5 is a process flow diagram illustrating the method of the present invention.

Referring to FIG. 1 there is shown generally by numeral 10 a catheter device specifically designed for use in a Monorail ™ catheter system for measuring blood pressure at locations within the vascular system of a living person or animal. The catheter itself comprises an elongated, relatively small diameter, flexible, plastic, bi-lumen tubular member 12 which is preferably formed in any one of a number of known extrusion techniques. For purposes of reference, the catheter 10 is shown as including a distal end 14 and a proximal end 16.

The two lumens of the bi-lumen catheter are identified by numerals 18 and 20, respectively. Formed through the wall of the tubular member 12 at a location only a few inches proximal of the distal end 14 of the catheter 10 is a guidewire port 22 which penetrates through so as to intersect with the lumen 18. With reference to the cross-sectional view of FIG. 3, which is taken along the line 3—3 just proximal of the guidewire port 22, it can be seen that a plug 24 is used to block the lumen 18. The lumen 20, however, is unobstructed from its distal end 14 to its proximal end 16. The same result can be achieved by using a single lumen tube for most of the catheter's length and then bonding a short, double-lumen segment, having an external port communicating with the added lumen to the distal end of the single lumen catheter. A molded plastic hub 26 is affixed to the proximal end 16 of the catheter to facilitate connecting the catheter to the particular electronics module used to take and record the pressure readings.

To facilitate positioning of the distal end 14 of the blood pressure monitoring catheter within the vascular system, using radioscopic techniques, a marker band 28 of a radiopaque material, such as gold, may be affixed to the catheter.

The blood pressure monitoring catheter may have an outside diameter of 1.2 mm and the lumens 18 and 20 may have a diameter of 0.3 mm and 0.4 mm, respectively. The port 22 may be displaced 10 cm from the distal end 14.

Referring now to FIGS. 4 and 5, the manner in which the blood pressure catheter of the present invention may be used is to be explained. In this regard, numeral 30 identifies a section of a blood vessel containing a stenotic lesion 32 on its inner wall. A guide catheter 34 has been introduced into the vascular system and routed through it until the distal end 36 thereof is as close as practical to the lesion to be treated. The guide catheter 34 has a guidewire 38 extending through its lumen and across the lesion 32.

When it is desired to take a pressure reading on the proximal side of the lesion 32, the blood pressure measuring catheter 10 is fitted onto the guidewire by inserting the proximal end of the guidewire 38 into the distal end of lumen 18 and advancing the catheter 10 along the guidewire until its proximal end hits the plug 24, whereupon the proximal end of the guidewire finds its way out of the guidewire port 22. Holding onto the proximal end of the guidewire 38, the surgeon next begins to feed the blood pressure monitoring catheter 12 down the lumen of the guide catheter 34 and the distal tip portion thereof will necessarily be constrained in its movement by the presence of the guidewire 38. Using fluoroscopic equipment, the surgeon will be able to discern when the distal tip with its marker band 28 is at a desired location relative to the stenotic lesion 32 for taking a measurement.

A similar reading may be taken after the blood pressure measuring catheter tip has been moved to the other side of the stenotic lesion. Knowing the two readings, the pressure gradient across lesion can be discerned. This may be done either prior to or after a dilation step to first determine the need for dilation and secondly to determine the efficacy of the dilation procedure.

Typically, the blood pressure measuring lumen 20 will be filled with an incompressible fluid, e.g., saline so that the blood pressure existing at the distal end of the catheter will be transmitted through the fluid to the proximal end 16 of the catheter and from there to the blood pressure measuring equipment (not shown). In alternative pressure catheters, a piezoelectric crystal functioning distal end of the catheter and the electrical conductors for driving the circuit and sensing variations due to pressure changes may extend through the catheter's lumen 20.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A pressure monitor catheter comprising:
   an elongated flexible plastic tubular member having a distal end and a proximal end with a pressure sensing lumen extending from said proximal end to a pressure sensing port located proximate said distal end and a guidewire lumen extending from said distal end to a guidewire port extending through the side wall of said tubular member at a location a relatively short predetermined distance proximal of said distal end, and an elongated guidewire extending exterior of said tubular member with a relatively short distal end portion of said guidewire extending through said guidewire port, said guidewire lumen and out said distal end of said tubular member.

2. The pressure monitor catheter as in claim 1 and further including a molded plastic hub attached to said proximal end of said tubular member for coupling said pressure sensing lumen to a blood pressure measuring apparatus.

3. The pressure monitor catheter as in claim 1 and further including radiopaque marker means disposed on said tubular member generally adjacent said distal end of said tubular member.

* * * * *